(12) United States Patent
Alba Rubio et al.

(10) Patent No.: US 11,607,677 B2
(45) Date of Patent: Mar. 21, 2023

(54) HOMOGENEOUS AND REUSABLE SUPERACID POLYMER CATALYST USEFUL FOR THE SYNTHESIS OF 5-HYDROXYMETHYLFURFURAL FROM GLUCOSE

(71) Applicant: The University of Toledo, Toledo, OH (US)

(72) Inventors: Ana C. Alba Rubio, Toledo, OH (US); Maria R. Coleman, Toledo, OH (US); Subhash Kalidindi, Toledo, OH (US); Anup S. Joshi, Toledo, OH (US); Ibeh S. Omodolor, Toledo, OH (US)

(73) Assignee: TJie University of Toledo, Toledo, OH (US)

( * ) Notice: Subject to any disclaimer, the term of this patent is extended or adjusted under 35 U.S.C. 154(b) by 359 days.

(21) Appl. No.: 16/759,065

(22) PCT Filed: Oct. 29, 2018

(86) PCT No.: PCT/US2018/057984
§ 371 (c)(1),
(2) Date: Apr. 24, 2020

(87) PCT Pub. No.: WO2019/089448
PCT Pub. Date: May 9, 2019

(65) Prior Publication Data
US 2020/0360910 A1 Nov. 19, 2020

Related U.S. Application Data

(60) Provisional application No. 62/578,659, filed on Oct. 30, 2017.

(51) Int. Cl.
| | |
|---|---|
| B01J 31/10 | (2006.01) |
| C01B 32/182 | (2017.01) |
| B01J 31/06 | (2006.01) |
| B01J 37/30 | (2006.01) |
| C07D 307/48 | (2006.01) |
| B82Y 30/00 | (2011.01) |
| B82Y 40/00 | (2011.01) |

(52) U.S. Cl.
CPC .......... B01J 31/10 (2013.01); B01J 31/069 (2013.01); B01J 37/30 (2013.01); C01B 32/182 (2017.08); C07D 307/48 (2013.01); B01J 2231/70 (2013.01); B82Y 30/00 (2013.01); B82Y 40/00 (2013.01)

(58) Field of Classification Search
CPC . B01J 31/10; B01J 31/069; B01J 37/30; B01J 2231/70; C01B 32/182; C07D 307/48; B82Y 30/00; B82Y 40/00
USPC ....................................................... 502/159
See application file for complete search history.

(56) References Cited

PUBLICATIONS

Gabriel Morales et al., "Sulfonic acid heterogeneous catalysts for dehydration of C6-monosaccharides to 5-hydroxymethlfurfural in dimethyl sulfoxide." Chinese Journal of Catalysis 35, pp. 644-655. (Year: 2014).*

(Continued)

*Primary Examiner* — Patricia L. Hailey
(74) *Attorney, Agent, or Firm* — MacMillan, Sobanski & Todd, LLC

(57) ABSTRACT

A superacid polymeric catalyst having both Lewis acidity and Brønsted acidity is described, along with methods of making and methods of using the same.

18 Claims, 10 Drawing Sheets

(56) References Cited

PUBLICATIONS

Yomaira J. Pagán-Torres et al., "Production of 5-Hydroxymethylfurfural from Glucose Using a Combination of Lewis and Brønsted Acid Catalysts in Water in a Biphasic Reactor with an Alkylphenol Solvent." ACS Catalysis, vol. 2, Issue 6, pp. 930-934. (Year: 2012).*

Jean Marcel R. Gallo et al., "Acid-functionalized mesoporous carbons for the continuous production of 5-hydroxymethylfurfural." Journal of Molecular Catalysis A: Chemical 422, pp. 13-17. (Year: 2016).*

V. L. Magnotta et al., "Superacide Polymers: Synthesis and Analysis of AlCl3-Sulfonic Acid Resin Complexes." Journal of Polymer Science, vol. 15, pp. 1341-1347. (Year: 1977).*

* cited by examiner

HOMOGENEOUS AND REUSABLE SUPERACID POLYMER CATALYST USEFUL FOR THE SYNTHESIS OF 5-HYDROXYMETHYLFURFURAL FROM GLUCOSE

CROSS-REFERENCE TO RELATED APPLICATIONS

This application is a national stage application filed under 35 U.S.C. § 371 of international application PCT/US2018/057984, filed under the authority of the Patent Cooperation Treaty on Oct. 29, 2018, which claims priority to U.S. Provisional Application No. 62/578,659 filed under 35 U.S.C. § 111(b) on Oct. 30, 2017, the disclosure of which is incorporated herein by reference in its entirety for all purposes.

STATEMENT REGARDING FEDERALLY SPONSORED RESEARCH

This invention was made with no government support. The government has no rights in this invention.

BACKGROUND OF THE INVENTION

The synthesis of 5-hydroxymethylfurfural (HMF) from glucose typically requires both Brønsted acid sites and Lewis acid sites. Lewis acid sites are responsible for the isomerization of glucose to fructose, while Brønsted acid sites are responsible for the dehydration of fructose to HMF. Thus, combinations of Brønsted and Lewis acid catalysts (for example, HCl and $AlCl_3$) are generally used to produce HMF from glucose. However, reutilization of such catalysts is complicated due to their solubility in the reaction medium. Heterogeneous catalysts containing both Brønsted acid sites and Lewis acid sites have also been prepared (for example, Sn—W oxide), but they are not usually as active as their homogeneous counterparts because not all active sites are exposed. Thus, there is a need in the art for new and improved catalysts for the production of HMF and other processes.

SUMMARY OF THE INVENTION

In a first broad aspect, described herein is a composition comprising Formula A:

Formula A

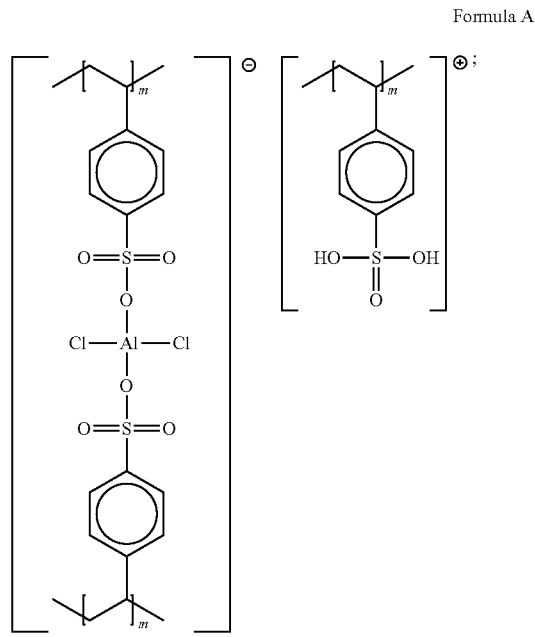

where m is an integer. In certain embodiments, m ranges from about 5,000 to about 85,000.

In certain embodiments, the polystyrene chain has a molecular weight from about 10,000 to about 1,500,000.

The composition is soluble in polar solvents. In certain embodiments, the composition is dissolved in a polar solvent selected from the group consisting of water, gamma-valerolactone (GVL), dimethyl sulfoxide (DMSO), and DMSO-water systems.

In certain embodiments, the composition is dissolved in a polar solvent comprising water, and a MIBK+2-butanol mixture is used as an organic phase for HMF extraction.

In certain embodiments, composition includes Brønsted acid sites and Lewis acid sites at a estimated Brønsted:Lewis ratio of up to about 90:10.

In certain embodiments, the estimated Brønsted:Lewis ratio is about 80:20.

In certain embodiments, the estimated Brønsted:Lewis ratio is about 70:30.

In certain embodiments, the estimated Brønsted:Lewis ratio is about 60:40.

In certain embodiments, the estimated Brønsted:Lewis ratio is about 50:50.

In certain embodiments, the estimated Brønsted:Lewis ratio is about 40:60.

In certain embodiments, the estimated Brønsted:Lewis ratio is about 30:70.

In certain embodiments, the estimated Brønsted:Lewis ratio is about 20:80.

In certain embodiments, the estimated Brønsted:Lewis ratio is about 10:90.

In certain embodiments, the composition further comprises nanoparticles, nanofibers, or nanosheets. In certain embodiments, the nanoparticles comprise alumina and/or carbon. In certain embodiments, the nanofibers comprise carbon. In certain embodiments, the nanosheets comprise graphene.

In certain embodiments, the composition further comprises a monomer which increases the hydrophilicity of the composition.

In another broad aspect, described herein is a composition comprising a poly(styrenesulfonic acid)-based (PSSA) polymer having both Lewis acid sites and Brønsted acid sites, wherein the composition is soluble in polar solvents.

In certain embodiments, the composition is made by ion exchange between PSSA and $AlCl_3$ in a liquid medium.

In certain embodiments, the composition is made by ion exchange between PSSA and one or more of $SnCl_4$, $TiCl_4$, $BF_3$, $MoS_2$, $ZnCl_2$, $VCl_4$, $NiCl_2$, $GaCl_3$, $GeCl_4$, $AsCl_2$, $BCl_3$, $SiCl_4$, $SbCl_3$, $PCl_3$, or $Et_2AlCl_3$.

In another broad aspect, described herein is a method of producing a catalyst, the method comprising adding a Lewis acid to soluble PSSA in a liquid medium to produce a superacid catalyst.

In certain embodiments, the Lewis acid is $AlCl_3$.

In certain other embodiments, the Lewis acid is one of $SnCl_4$, $TiCl_4$, $BF_3$, $MoS_2$, $ZnCl_2$, $VCl_4$, $NiCl_2$, $GaCl_3$, $GeCl_4$, $AsCl_2$, $BCl_3$, $SiCl_4$, $SbCl_3$, $PCl_3$, or $Et_2AlCl_3$.

In certain embodiments, the liquid medium comprises a mixture of methanol and ethanol.

In certain embodiments, the mixture comprises a ratio of methanol:(methanol+ethanol) ranging from about 0.5 to about 0.75 by volume.

In certain embodiments, the ratio is about 0.6 methanol:(methanol+ethanol) by volume.

In another broad aspect, described herein is a method of preparing 5-hydroxymethylfurfural (HMF), where the method comprises isomerizing glucose to fructose and dehydrating fructose in a feedstock with a single catalyst to produce HMF, wherein the catalyst comprises a poly(styrenesulfonic acid)-based (PSSA) polymer having both Lewis acid sites and Brønsted acid sites.

In certain embodiments, the catalyst comprises Formula A:

Formula A

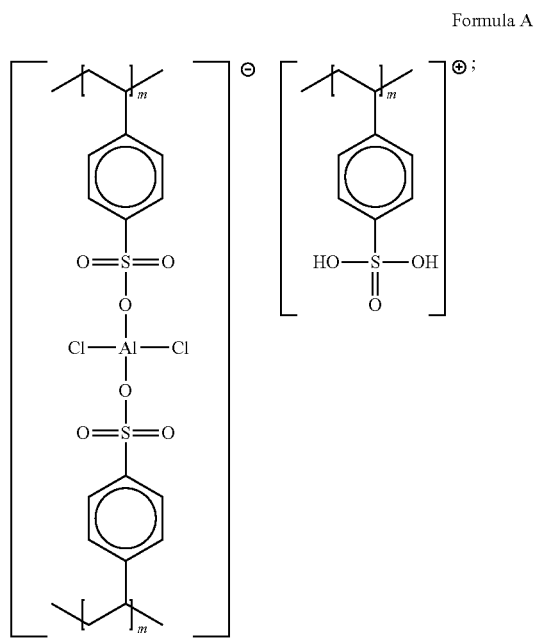

where m is an integer.

In certain embodiments, the polystyrene chain has a molecular weight from about 10,000 to about 1,500,000.

In certain embodiments, m ranges from about 5,000 to about 85,000.

In certain embodiments, the isomerization and dehydration are conducted in a solvent comprising water, gamma-valerolactone (GVL), dimethyl sulfoxide (DMSO), a water-DMSO system, or in a biphasic aqueous-organic system comprising water-(MIBK+2-butanol).

In certain embodiments, the method further comprises converting the HMF into one of dimethylfuran (DMF), adipic acid, 1,6-hexanediol, levulinic acid, caprolactam, 2,5-dimethylfuran, 5-hydroxymethylfuronic acid, 3,5-dihydroxymethylfuran, 5-hydroxy-4-keto-2-pentenoic acid, or 2,5-furandicarboxylic acid (FDCA).

In certain embodiments, the feedstock comprises a mixture of the glucose with fructose.

In another broad aspect, described herein is a method of making a catalyst, where the method comprises:

i) dissolving PSSA in anhydrous methanol to form a PSSA-methanol solution;

ii) dissolving $AlCl_3$ in anhydrous ethanol to form an $AlCl_3$-ethanol solution;

iii) adding the $AlCl_3$-ethanol solution to the PSSA-methanol solution to create a mixture;

iv) stirring the mixture for a period; and v) filtering the mixture with a membrane to separate the catalyst.

In certain embodiments, the membrane comprises polyethersulfone.

In certain embodiments, the method further comprises stirring one or both of the PSSA-methanol solution and the $AlCl_3$-ethanol solution prior to the adding step iii).

In certain embodiments, the method further comprises adjusting the amount of $AlCl_3$ dissolved in the anhydrous ethanol to adjust the amount of Lewis acid sites in the catalyst.

In certain embodiments, the mixture comprises a ratio of methanol:(methanol+ethanol) ranging from about 0.5 to about 0.75 by volume.

In another broad aspect, described herein is a solution comprising soluble $AlCl_3$ and soluble polystyrenesulfonic acid (PSSA) in a mixture of ethanol and methanol, where the mixture comprises a ratio of methanol:(methanol+ethanol) ranging from about 0.5 to about 0.75 by volume, the $AlCl_3$ is present at a concentration of at least 0.001 g/mL mixture, and the PSSA is present at a concentration of at least 0.012 g/mL mixture.

In certain embodiments, the solution has the ratio of methanol:(methanol+ethanol) about 0.6 by volume.

In another broad aspect, described herein is a kit for making a catalyst having a first container housing a PSSA polymer; and a second container housing $AlCl_3$. In certain embodiments, the kit further includes at least one solvent.

BRIEF DESCRIPTION OF THE DRAWINGS

FIG. 9A shows fructose conversion, and FIG. 9B shows HMF yield. Conditions: (MIBK+2-butanol): water=(6.3 mL+2.7 mL): 1.5 mL, 150 mg fructose, 150° C., 1000 rpm, (32.4 mg PSSA, 34.0 mg Amberlyst®, 1.5 mL of a 0.06 M $H_2SO_4$ solution, all corresponding to 0.175 mmol $H^+$). Lines have been added to guide the eye. FIG. 9C shows turnover frequencies for production of HMF with PSSA catalyst: Reutilization experiment. Conditions: (MIBK+2-butanol): water=(4.2 mL+1.8 mL): 3 mL, 300 mg fructose, 150° C., 940 rpm, 100 mg PSSA, 30 min. The red line in FIG. 9C represents the mean value±standard deviation for the six runs.

FIG. 10A shows glucose conversion, and FIG. 10B shows HMF yield. Conditions: (MIBK+2-butanol): water=(6.3 mL+2.7 mL): 1.5 mL, 150 mg glucose, 150° C., 1000 rpm, (32.4 mg PSSA, 35 mg PSSA-AlCl$_3$ 90:10, 37.8 mg PSSA-AlCl$_3$ 80:20, 38 mg PSSA-AlCl$_3$ 70:30, 39.5 mg PSSA-AlCl$_3$ 60:40, 40 mg PSSA-AlCl$_3$ 50:50, 42.7 mg PSSA-AlCl$_3$ 40:60, 44.5 mg PSSA-AlCl$_3$ 30:70, 64.6 mg PSSA-AlCl$_3$ 20:80, all corresponding to 0.175 mmol H$^+$). Lines have been added to guide the eye. FIG. 10C shows turnover frequencies for production of HMF with PSSA 70:30 catalyst:Reutilization experiment. Conditions: (MIBK+2-butanol): water=(4.2 mL+1.8 mL): 3 mL, 300 mg glucose, 150° C., 940 rpm, 140 mg PSSA-AlCl$_3$ 70:30, 2 h. The red line in FIG. 10C represents the mean value±standard deviation for the five runs.

DETAILED DESCRIPTION

The disclosures of these publications, patents, and published patent specifications are hereby incorporated by reference into the present disclosure in their entirety to more fully describe the state of the art to which this invention pertains.

Provided is a reusable polymer catalyst containing both Brønsted and Lewis acid sites. The catalyst has been demonstrated to be effective in the production of 5-hydroxymethylfurfural from glucose in a one-pot synthesis. The catalyst is further useable in a wide variety of other applications (e.g., synthesis of furfural from xylose).

Figure 2A:
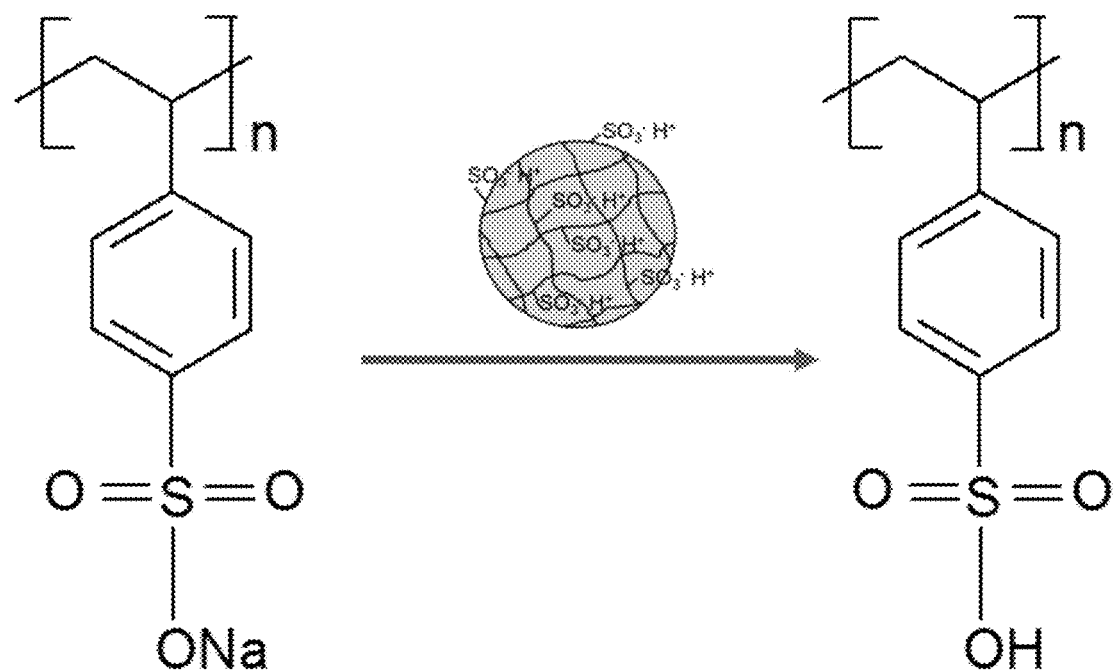
FIGS. 2A-2B: Synthesis of polystyrene sulfonic acid (PSSA) by ion exchange of sodium polystyrene sulfonate (PSSS) with a sulfonic resin (FIG. 2A), and photograph of the PSSA so obtained (FIG. 2B).

Poly(styrenesulfonic acid) (PSSA) combines the advantages of both homogeneous and heterogeneous catalysis. PSSA is soluble in polar solvents. Therefore, all acidic sulfonic groups are readily accessible. In addition, PSSA cannot be deactivated through coking because there is no surface for the carbonaceous species to be deposited. Heterogeneous catalysts are generally subjected to coking. At the same time, PSSA, due to its high molecular weight, can be easily recovered by ultrafiltration for further utilization. PSSA can be prepared by, for instance, by ion exchange of sodium polystyrenesulfonate (PSSS) with a sulfonic resin, as depicted in FIG. 2A. PSSA can be obtained by sulfonation of polystyrene waste (e.g., yogurt packaging or expanded polystyrene), which is an additional advantage from an environmental point of view. This polymer catalyst demonstrated high activity in several biomass conversion reactions that require Brønsted acid sites, such as: synthesis of biodiesel from vegetable oil, dehydration of xylose to furfural, and furfural oxidation to maleic and succinic acids. However, in the context of HMF production from glucose, PSSA can catalyze the dehydration step, but generally only to a limited extent the isomerization step, and thus is not used as the only catalyst to produce HMF from glucose.

In accordance with the present disclosure, Lewis acid functionality is added to PSSA to create a superacid catalyst, PSSA-AlCl$_3$. In general, the PSSA-AlCl$_3$ catalyst composition has the structural formula of Formula A:

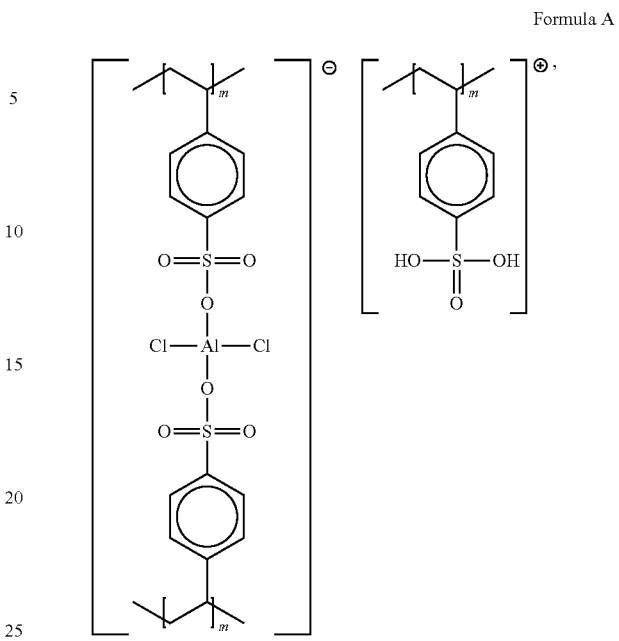

Formula A m ranges from about 5,000 to about 85,000. In certain embodiments, the polystyrene chain has a molecular weight from about 10,000 to about 1,500,000. However, it is understood that other values m are entirely possible and encompassed within the scope of the present disclosure. The superacid catalyst is useful, for instance, for catalyzing a one-pot synthesis of hydroxymethylfurfural (HMF) from glucose in a reusable manner.

Although PSSA-AlCl$_3$ is described for exemplary purposes, Lewis acid functionality can be added to PSSA through the addition of Lewis acid sites other than AlCl$_3$. For example, Lewis acid sites can be incorporated into PSSA using Lewis acids such as SnCl$_4$, TiCl$_4$, BF$_3$, MoS$_2$, ZnCl$_2$, VCl$_4$, NiCl$_2$, GaCl$_3$, GeCl$_4$, AsCl$_2$, BCl$_3$, SiCl$_4$, SbCl$_3$, PCl$_3$, Et$_2$AlCl$_3$, or the like, in the same manner as described herein for AlCl$_3$ (i.e., ion exchange) to similarly produce superacid catalysts. Though AlCl$_3$ is described herein for illustrative purposes, such other catalysts are encompassed within the present disclosure.

Since PSSA already contains Brønsted acid groups, Lewis acid sites are added to PSSA to synthesize a superacid polymer catalyst (e.g., PSSA-AlCl$_3$) useful for conversion of glucose to HMF via one-pot synthesis. The PSSA-AlCl$_3$ catalyst is soluble in polar solvents (i.e., is homogeneous) with high molecular weight for an easy recovery by ultrafiltration for further reutilization. Moreover, the number of active sites on the catalyst can be customized. It is to be noted that, as used herein "estimated" means "theoretical based on the amounts added." For example, in certain embodiments, Formula A includes a estimated Brønsted: Lewis ratio of about 10:90, about 20:80, about 30:70, about 40:60, about 50:50, about 60:40, about 70:30, about 80:20, or about 90:10. The ratio of Brønsted:Lewis sites can be customized for the desired application.

Figure 1:
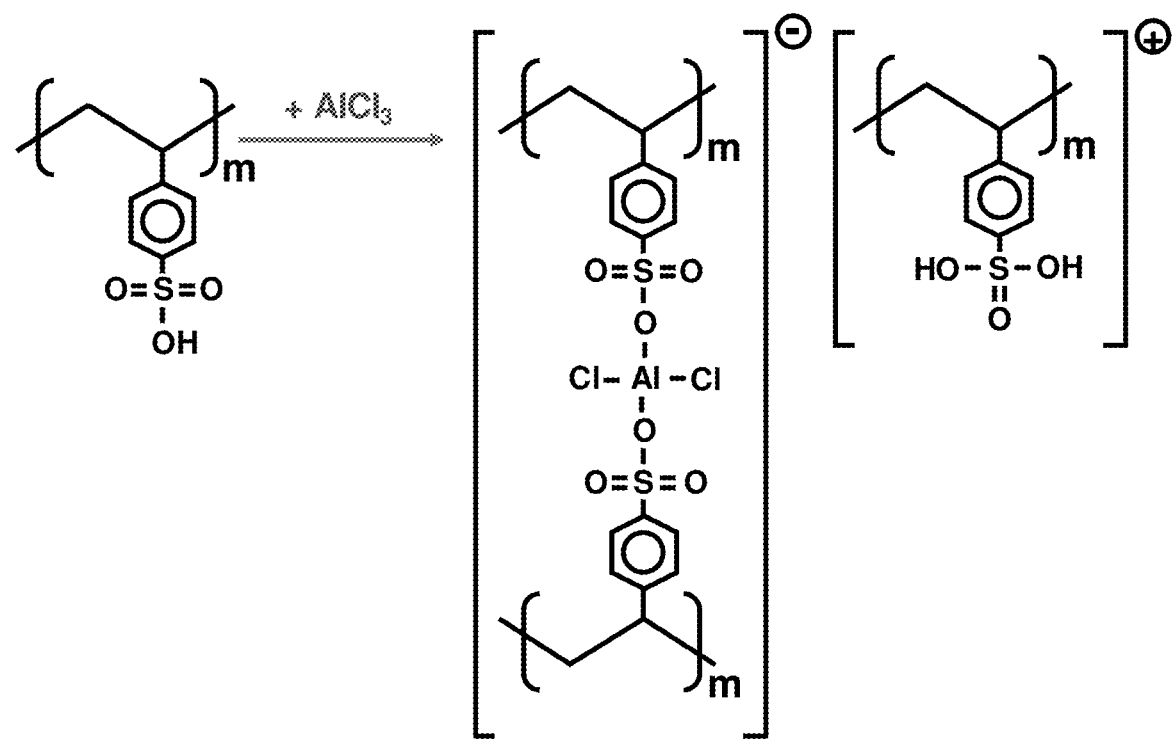
FIG. 1: Production of PSSA-$AlCl_3$ (Formula A) through ion exchange between PSSA and $AlCl_3$.

Formula A can be prepared through the addition of AlCl$_3$ to soluble poly(styrenesulfonic acid) (PSSA) by ion exchange in liquid medium. (FIG. 1.) PSSA may be obtained by sulfonation of polystyrene waste or by ion exchange of polystyrene sulfonate, such as poly(sodium-4-styrenesulfonate) (PSSS) with a sulfonic resin or H$_2$SO$_4$. PSSA is a soluble polymer containing only Brønsted acid sites that has demonstrated high activity in several biomass conversion reactions, namely, synthesis of biodiesel from vegetable oil, dehydration of xylose to furfural, and furfural oxidation to maleic and succinic acids. Sulfonic resins have previously had Lewis acid sites incorporated. However, such previous catalysts were not soluble in polar solvents.

An acid resin, such as, but not limited to, Amberlyst 15®, may be used as a sulfonic resin for ion exchange to produce PSSA from PSSS. For example, Amberlyst 15® may be added to a solution of PSSS. The sulfonic resin can then be removed from the solution by filtration, leaving behind a PSSA solution that can be heated to evaporate water in order to recover solid PSSA. The solid PSSA can be dissolved in a solvent such as methanol, and optionally subjected to ultrafiltration (such as with a polyethersulfone membrane) to remove polymer chains having a smaller than desired size. Other methods of producing PSSA for ion exchange with $AlCl_3$ are possible and entirely encompassed within the present disclosure.

To conduct the ion exchange between $AlCl_3$ and PSSA, $AlCl_3$ is dissolved in a suitable solvent, such as ethanol, to form a solution, and this $AlCl_3$ solution is added to a solution of PSSA in a suitable solvent, such as methanol. Optionally, this is conducted dropwise with constant stirring. Stirring may continue for a period of time, such as several hours, at room temperature after the solutions have been fully combined, in order to complete the ion exchange. Once completed, the mixture can be subjected to ultrafiltration, such as with a polyethersulfone membrane, and dried to recover PSSA-$AlCl_3$. In order to adjust the ratio of Brønsted:Lewis sites in the product, different amounts of $AlCl_3$ are used in the ion exchange.

Notably, $AlCl_3$ is not soluble in methanol, but the PSSA polymer is. Furthermore, PSSA is not very soluble in ethanol, though $AlCl_3$ is. Accordingly, a mixture of ethanol and methanol may be used to solubilize both $AlCl_3$ and PSSA for the ion exchange to prepare Formula A. In some embodiments, this mixture is at a methanol:(methanol+ethanol) ratio ranging from about 0.5 to about 0.75 by volume. In one non-limiting example, the mixture comprises a 0.6 ratio by volume of methanol:(methanol+ethanol). However, other methods of adding $AlCl_3$ to the soluble PSSA are possible and entirely encompassed within the scope of the present disclosure. Furthermore, in order to maintain the solubility of the polymer for an increased performance, the degree of sulfonation is typically kept above 30% when adding the Lewis acid functionality. However, it is understood that this is not strictly necessary to produce Formula A.

Homogeneous catalysts are generally more active than their heterogeneous counterparts because their solubility in the reaction medium contributes to access of reactants to all active sites. However, heterogeneous catalysts are commonly preferred because heterogeneous catalysts can be easily recovered from the reaction medium and be reused. The catalyst of Formula A combines the advantages of both homogeneous and heterogeneous catalysts. The catalyst of Formula A is soluble in polar solvents; therefore, it acts as a homogeneous catalyst, and all the acid sites are easily reachable and exposed for catalysis. At the same time, being soluble means the catalyst of Formula A cannot be deactivated through coking because there is no physical surface for the carbonaceous species to be deposited. This is especially important for biomass conversion reactions, since this mode of deactivation is a very common problem. Furthermore, due to its high molecular weight, the catalyst of Formula A can be easily recovered by ultrafiltration to be reused.

Non-limiting examples of polar solvents that Formula A is soluble in include water, methanol, gamma-valerolactone (GVL), dimethyl sulfoxide (DMSO), and water-DMSO systems. Advantageously, GVL is also considered a green solvent. In one non-limiting example, the reaction is carried out in an aqueous-organic biphasic system. In one non-limiting example, the catalyst of Formula A is dissolved in water with a combination of MIBK and 2-butanol as the organic phase for HMF extraction. In another non-limiting example, the catalyst of Formula A is dissolved in a solvent composed of a DMSO-water system.

Figure 3:
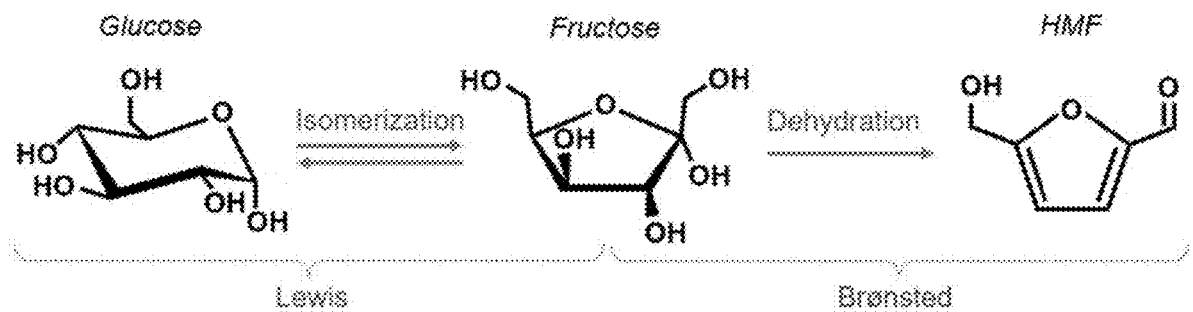
FIG. 3: Conversion of glucose to HMF by a combined isomerization/dehydration pathway.

There are many types of reactions that benefit from a homogeneous and reusable catalyst having both Brønsted and Lewis acid functionalities. One non-limiting example is the production of 5-hydroxymethylfurfural (HMF) from glucose, which requires Lewis acid sites for isomerization of glucose to fructose, and Brønsted acid sites for dehydration of fructose to HMF. (FIG. 3.) As described below, the effectiveness of the catalyst of Formula A has been demonstrated in this tandem reaction. However, the catalyst of Formula A may be employed as a catalyst in any reaction which involves an acid catalyst, including, but not limited to, esterifications, isomerizations, alkylations, polymerizations, cracking reactions, acylations, etherifications, acetalizations, nitrations, and disproportionations.

As noted above, the catalyst of Formula A can be recovered from a reaction medium through methods such as ultrafiltration. Ultrafiltration is a type of membrane filtration in which pressure forces a liquid against a semipermeable membrane, which is a thin layer of material capable of separating substances when a driving force is applied across it. Ultrafiltration is applied in a variety of applications, but mainly in the filtration of biomolecules of interest in medical and biochemical applications. Its viability has also been shown in polymer applications. Once the polymer is retained in the membrane, it can be liberated by re-dissolution in the reaction medium and be reutilized provided that the catalyst is not deactivated during use. The membranes here used for ultrafiltration can recover catalysts with a molecular weight as low as about 5 kDa. As shown in the examples herein, the catalyst of Formula A can be recovered from reaction media by ultrafiltration and reused without deactivation.

Formula A may be further modified in a variety of ways encompassed within the present disclosure. For example, PSSA-$AlCl_3$ may be obtained by addition of $AlCl_3$ leading to crosslinking (Formula A) or by copolymerization of monomers containing Brønsted and Lewis acid sites. Further, PSSA-$AlCl_3$ may be anchored to nanoparticles, nanofibers, or nanosheets to allow for conventional filtration for easier recovery. The solubility of the polymer chains on the reaction medium eliminates the deactivation by coking. Additionally, PSSA-$AlCl_3$ can be modified with monomers that improve the hydrophilicity of the material. This helps increase the amount of Lewis acid sites on the polymer while maintaining it soluble, which improves, for example, the synthesis of HMF from glucose.

HMF can be produced from glucose by a tandem reaction which involves the isomerization of glucose to fructose followed by the dehydration of fructose to HMF. (FIG. 3.) A one-pot synthesis of HMF involves the isomerization of glucose to fructose in the presence of a Lewis acid catalyst followed by the dehydration of fructose to HMF using a Brønsted acid catalyst. The most common Lewis acid catalysts conventionally used in this reaction are $AlCl_3$, $SnCl_4$, CrCl$_3$, GaCl$_3$, InCl$_3$, and YbCl$_3$, among others. On the other hand, mineral acids such as HCl and H$_2$SO$_4$, zeolites, and sulfonic resins have been used as a source of Brønsted acid sites. For the synthesis of HMF from glucose, combinations of both Lewis and Brønsted acid sites are typically used, as well as catalysts containing both functionalities.

H$_2$SO$_4$ is a very active catalyst for the dehydration of fructose to HMF, but it cannot be reused due to its homogeneous nature. Similarly, AlCl$_3$ cannot be easily recovered and reused because it is dissolved in the reaction medium. For this reason, heterogeneous catalysts are usually preferred. Among the heterogeneous acid catalysts containing —SO$_3$H groups, Amberlyst 15®, Amberlyst 70®, Amberlyst 38®, and Dowex® have been used to convert fructose into HMF due to their large number of Brønsted acid sites (—SO$_3$H). However, the major drawback of sulfonic resins is that they deactivate through leaching and/or coking when used in reactions at high temperature and pressure. In addition, to match the number of acid sites with that on sulfuric acid, large amounts of sulfonic resins are required in the reaction.

Amberlyst 15® and Amberlyst 70® have also shown promising results in the presence of other solvents, such as dimethylformamide (DMF), tetrahydrofuran (THF), water, dioxane, and ionic liquids. However, a disadvantage of carrying out this reaction only in an aqueous phase is that products of hydration of HMF, such as formic and levulinic acids, are easily formed. The addition of poly(1-vinyl-2-pyrrolidinone) (PVP) or DMSO to the system reduces the amount of side products formed. In addition to sulfonic resins, other heterogeneous catalysts such as zeolites, mesoporous catalysts, and polymer catalysts containing sulfonic groups have been used.

Although fructose is commonly used to produce HMF, glucose is preferred over fructose due to its higher abundance and lower cost compared to fructose. Thus, the production of HMF in one-pot from glucose instead of from fructose is more cost-effective. This efficiency is amplified by the fact that the PSSA-AlCl$_3$ catalyst is recoverable and reusable. The PSSA-AlCl$_3$ catalyst of Formula A is capable of catalyzing this one-pot synthesis of HMF from glucose. Furthermore, because Formula A can catalyze both the isomerization of glucose to fructose and the dehydration of fructose to HMF, Formula A can be used to produce HMF from a feedstock that contains a mixture of glucose and fructose. The one-pot synthesis can be conducted in, for example, solvents such as water, GVL, DMSO, or a mixture of DMSO and water. However, an aqueous-organic biphasic system, such as water-(MIBK+2-butanol) is advantageous for extracting HMF as soon it is formed to minimize the occurrence of side reactions. In such solvents, the PSSA-AlCl$_3$ catalyst of Formula A is soluble and the reaction can proceed more efficiently.

Figure 4:
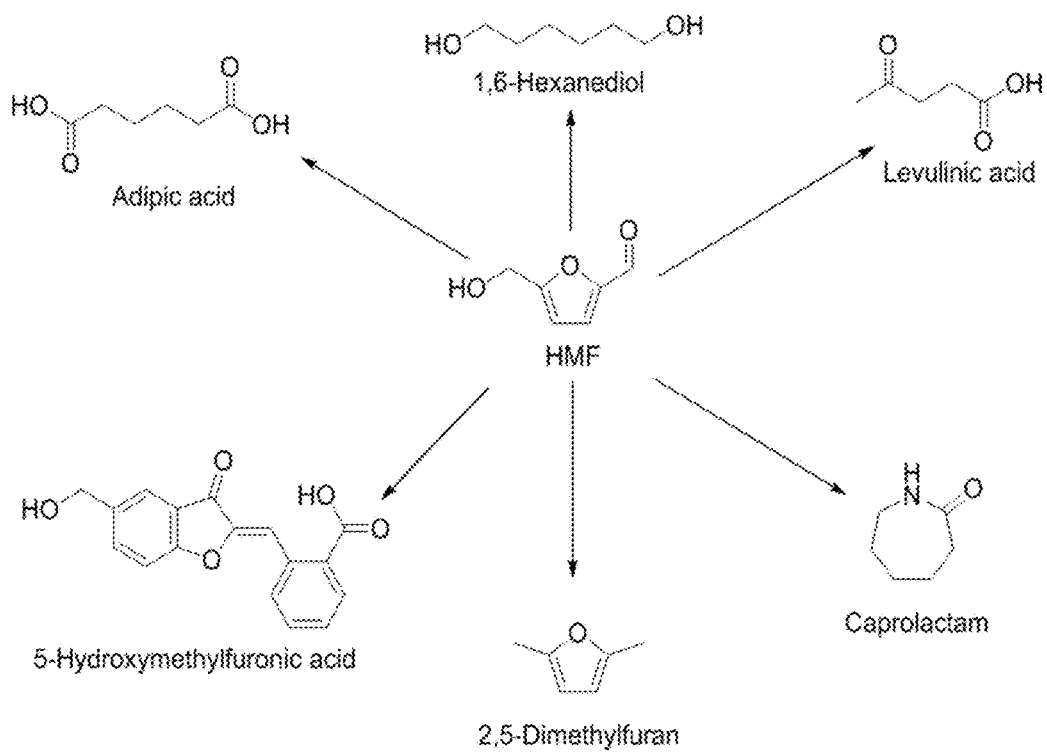
FIG. 4: Non-limiting example compounds made from HMF.

HMF is a platform molecule, useful for producing a variety of valuable chemicals. (FIG. 4.) HMF, together with furfural and 2,5-furandicarboxylic acid (FDCA), are derivatives of furan compounds which are among the top value-added bio-based chemicals currently produced. HMF derivatives, such as FDCA as a substitute of terephthalic acid in the PET industry, or adipic acid for the nylon industry, are in demand. HMF is also useful as an intermediate for the production of the biofuel dimethylfuran (DMF) and other molecules such as levulinic acid, 2,5-diformylfuran, 3,5-dihydroxymethylfuran, and 5-hydroxy-4-keto-2-pentenoic acid. Thus, the method of preparing HMF described herein can be but one step of a multi-step synthesis for a plethora of downstream products.

The compositions and methods described herein may be embodied as parts of a kit or kits. A non-limiting example of such a kit is a kit for making a catalyst of Formula A, the kit comprising a PSSA polymer and AlCl$_3$ in separate containers, where the containers may or may not be present in a combined configuration. Many other kits are possible, such as kits further comprising at least one solvent for solubilizing PSSA and/or AlCl$_3$, and/or at least one polar solvent for dissolving a PSSA-AlCl$_3$ catalyst. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example I—Synthesis and Characterization of PSSA-AlCl$_3$

Sulfonic groups in PSSA were partially replaced by AlCl$_3$ while maintaining a degree of sulfonation higher than 30% to keep the polymer soluble in reaction medium for HMF production from glucose. The result was a superacid PSSA-AlCl$_3$ catalyst produced in liquid medium under inert atmosphere at room temperature.

Preparation of PSSA-AlCl$_3$ Superacid Catalyst by Ion Exchange

Figure 2B:
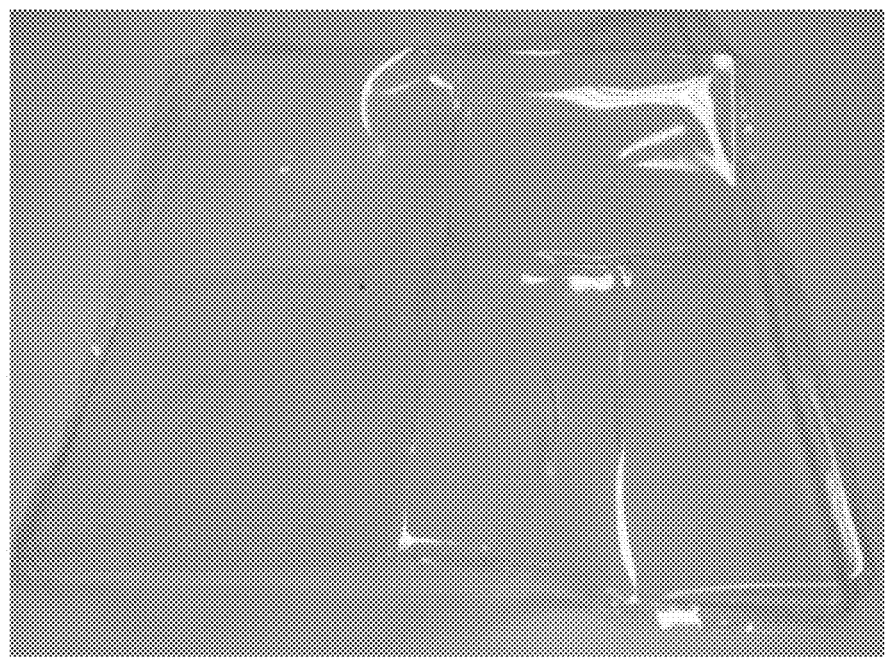

PSSA was prepared from poly(sodium-4-styrene-sulfonate) (PSSS) (supplied by Sigma-Aldrich (25 wt %, approx. MW of the polymer 200 kDa)) as the precursor. The PSSS was transformed to PSSA by ion exchange using an acid resin, Amberlyst 15® (H$^+$ capacity=4.7 meq·g$^{-1}$). 120 g of Amberlyst 15® was crushed and added into 600 mL of an aqueous solution of PSSS. The mixture was stirred overnight at room temperature to maximize the exchange (FIG. 2A). The sulfonic resin was then removed from the solution by conventional filtration. The filtered PSSA solution obtained was then heated in an oven for 8 h at 70° C. to evaporate water. The dried solid was then dissolved in about 900 mL of methanol under vigorous stirring until dissolution. The PSSA-methanol solution was subjected to ultrafiltration using a 5 kDa polyethersulfone membrane (Millipore Biomax) to remove polymer chains of smaller size. The first step of the ultrafiltration technique involved removing the glossy glycerine layer present on the membrane by passing about 700 mL of water through it. The second step involved the ultrafiltration of the methanol-PSSA solution through the same 5 kDa membrane in a cell pressurized to 25 psi with N$_2$ under stirring. The ultrafiltered PSSA solution was dried overnight at 50° C. A photograph of the PSSA obtained after drying is shown in FIG. 2B.

To carry out the ion exchange with AlCl$_3$ in liquid phase under inert atmosphere, PSSA was dissolved in anhydrous methanol and AlCl$_3$ was dissolved in anhydrous ethanol. Notably, the solubility of PSSA in ethanol and the solubility of AlCl₃ in methanol are each low. To better understand the solubility of both PSSA and AlCl₃ in mixtures of methanol and ethanol, some preliminary experiments were carried out first. All the experiments were performed in a VAC glovebox to ensure that AlCl₃ was not oxidized or hydrated to form either $Al_2O_3$ or $AlCl_3 \cdot 6H_2O$. The volume of ethanol used was fixed and the amount of methanol was varied, as well as the amount of PSSA or AlCl₃ dissolved. Using the results of these experiments, a phase diagram was drawn (FIG. 5) and the region in which both PSSA and AlCl₃ were soluble in the ethanol-methanol mixture was taken as the optimum to carry out the ion exchange. The use of this methanol:ethanol ratio avoids the precipitation or formation of emulsions, making the ion exchange more efficient. Once the methanol:ethanol ratio was optimized, PSSA was dissolved in the appropriate amount of anhydrous methanol, and AlCl₃ was dissolved in anhydrous ethanol, in separate vials. To maintain a uniform solubility, the PSSA-methanol and AlCl₃-ethanol solutions were independently stirred for 1 h. Then, the AlCl₃-ethanol solution was added to the PSSA-methanol solution dropwise using a peristaltic pump at a rate of 0.6 mL/min under stirring at 1000 rpm. The mixture was then stirred for 3 h at room temperature for the ion exchange to take place. Once completed, the mixture was ultrafiltered using a 5 kDa Biomax polyethersulfone membrane. The retentate was dried overnight at 50° C. The appearance of PSSA-AlCl₃ was similar to that of PSSA but its color was less intense.

Thermogravimetric Analysis (TGA) of PSSA-AlCl₃ Catalysts

TGA of PSSA-AlCl₃ samples were carried out at the Center for Materials and Sensor Characterization (CMSC) of the University of Toledo using a TA TGA instrument with a heating ramp of 10° C./min starting from room temperature to 800° C. under flow of nitrogen. ~7 mg of catalyst was used to analyze the thermal properties of these materials.

Amount of BrøNsted Acid Sites in PSSA-AlCl₃ Catalysts

The amount of Brønsted acid sites on the PSSA-AlCl₃ catalysts was analyzed using acid-base titration with 0.1 N NaOH. The NaOH solution was first standardized using potassium phthalate. 15 mg of PSSA-AlCl₃ catalyst was dissolved in approximately 10 mL of water and titrated against NaOH solution using phenolphthalein as an indicator. Different catalysts with varied Brønsted:Lewis acid site ratios were obtained by using different amounts of AlCl₃. Samples were labelled as PSSA-AlCl₃ B:L, where B stands for the estimated percentage of Brønsted acid sites present in the catalyst and L stands for the number of Brønsted acid sites estimatedly substituted by Lewis acid sites by ion exchange.

¹H and ¹³C NMR of PSSA-AlCl₃ Catalysts

¹H and ¹³C NMR of PSSA-AlCl₃ catalysts were performed at the Instrumentation Center of the University of Toledo using a Bruker AVANCE-600 NMR equipment. Samples for ¹H NMR were prepared by dissolving 20 mg of PSSA-AlCl₃ in 0.5 mL of deuterated methanol under stirring for 1 h. The parameters of operation for ¹H NMR were AQ mode: DQD, TD: 65536; DS: 2, AQ: 2.72, NS: 16.

Samples for ¹³C NMR sample were prepared by dissolving 20 mg of PSSA-AlCl₃ in 0.5 mL of deuterated water under stirring for 1 h. The parameters of operation for ¹³C NMR were SW, 250 ppm, TD: 65536; DS: 20, AQ: 0.98, NS: 1024.

Attenuated Total Reflection (ATR) Analysis of PSSA-AlCl₃ Catalysts

PSSA-AlCl₃ samples were characterized by ATR at the Center for Materials and Sensor Characterization at the University of Toledo. ~0.5 mm thin sheets of PSSA and PSSA-AlCl₃ samples were placed on the equipment and analyzed using ATR with a germanium tip and 124 scans. PSSA-AlCl₃ samples were dried under vacuum overnight prior to analysis.

Inductively Coupled Plasma-Mass Spectrometry (ICP-MS) Analysis of PSSA-AlCl₃ Catalysts The amount of Al incorporated into the polymer and the success of the ion exchange were evaluated using an ICP-MS technique. In a typical analysis, ~55 mg of each sample was digested in HNO₃ using a CEM Mars microwave. After digestion, samples were filtered to remove particulate material. The filtrate was diluted to 3.5% HNO₃ for analysis in ICP-MS (X series 2, Thermo Scientific, MA USA). For quantitative analysis, standards were prepared by using certified ICP-MS standards from Inorganic Ventures. Correlation coefficients for calibration curves were above 0.999.

Results and Discussion

Phase Diagram to Optimize the Ion Exchange in Liquid Medium

Figure 5:
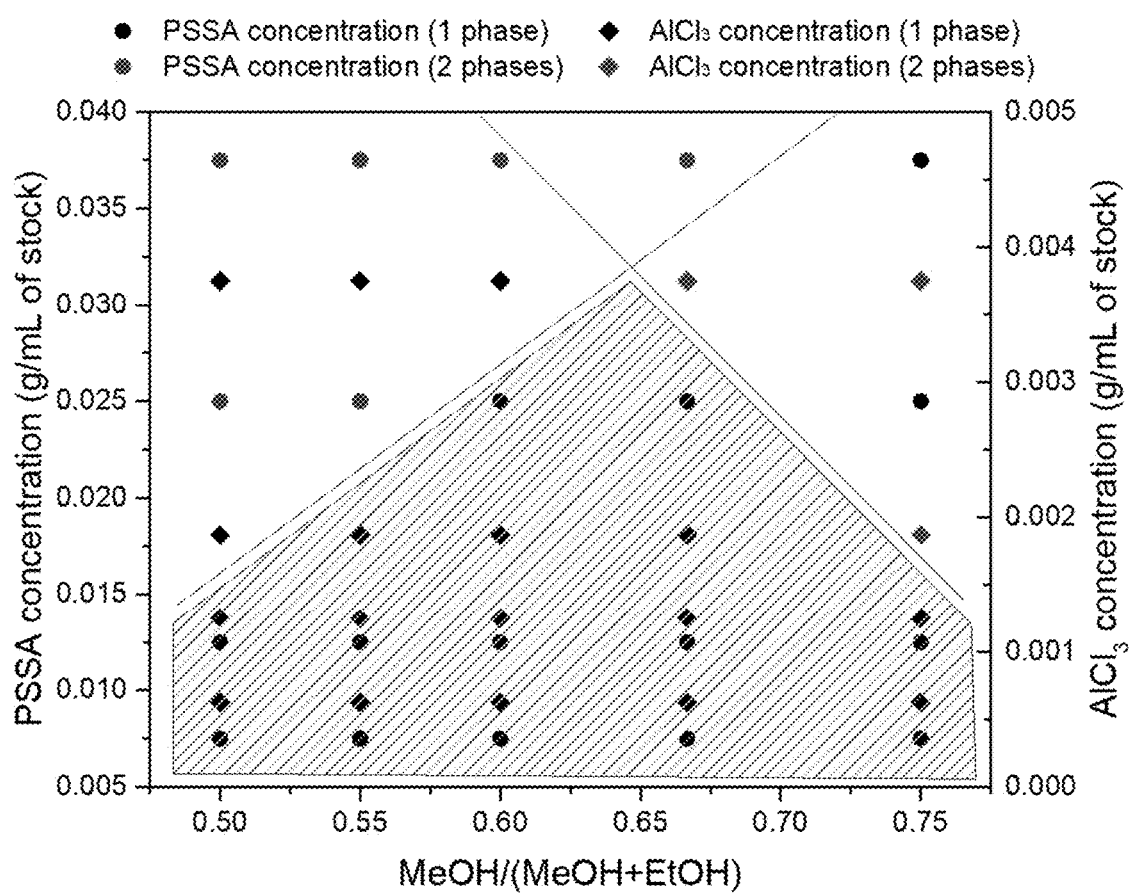
FIG. 5: Phase diagram to optimize the methanol:ethanol volume ratio for an effective ion exchange. Stock: methanol+ethanol total volume.

Since PSSA is soluble in methanol (but insoluble in ethanol), and AlCl₃ is soluble in ethanol but slightly soluble in methanol, the optimum liquid mixture to carry out the ion exchange without precipitation or formation of emulsions that would reduce the efficiency of the process was determined. The volume of ethanol was fixed and different volumes of methanol were added. The solubility of PSSA and AlCl₃ independently on those mixtures was evaluated, and a phase diagram was drawn (FIG. 5). The region in which only one phase is observed for both the dissolution of PSSA and AlCl₃ (green area) can be clearly seen in the phase diagram. 0.6 was chosen as the volume ratio for the ion exchange, while using different volumes of methanol and ethanol to keep the polymer soluble during ion exchange. Catalysts with different estimated B:L acid sites ratios (90:10, 80:20, 70:30, 60:40, 50:50, 40:60, 30:70, and 20:80) were prepared. To do so, the amount of PSSA was fixed to 1 g and the amount of anhydrous AlCl₃ used varied between 36 and 290 mg. The volume of methanol used varied between 48 mL and 384 mL, and the volume of ethanol between 32 and 256 mL.

Thermogravimetric Analysis of PSSA and PSSA-AlCl₃ Catalysts

Figure 6:
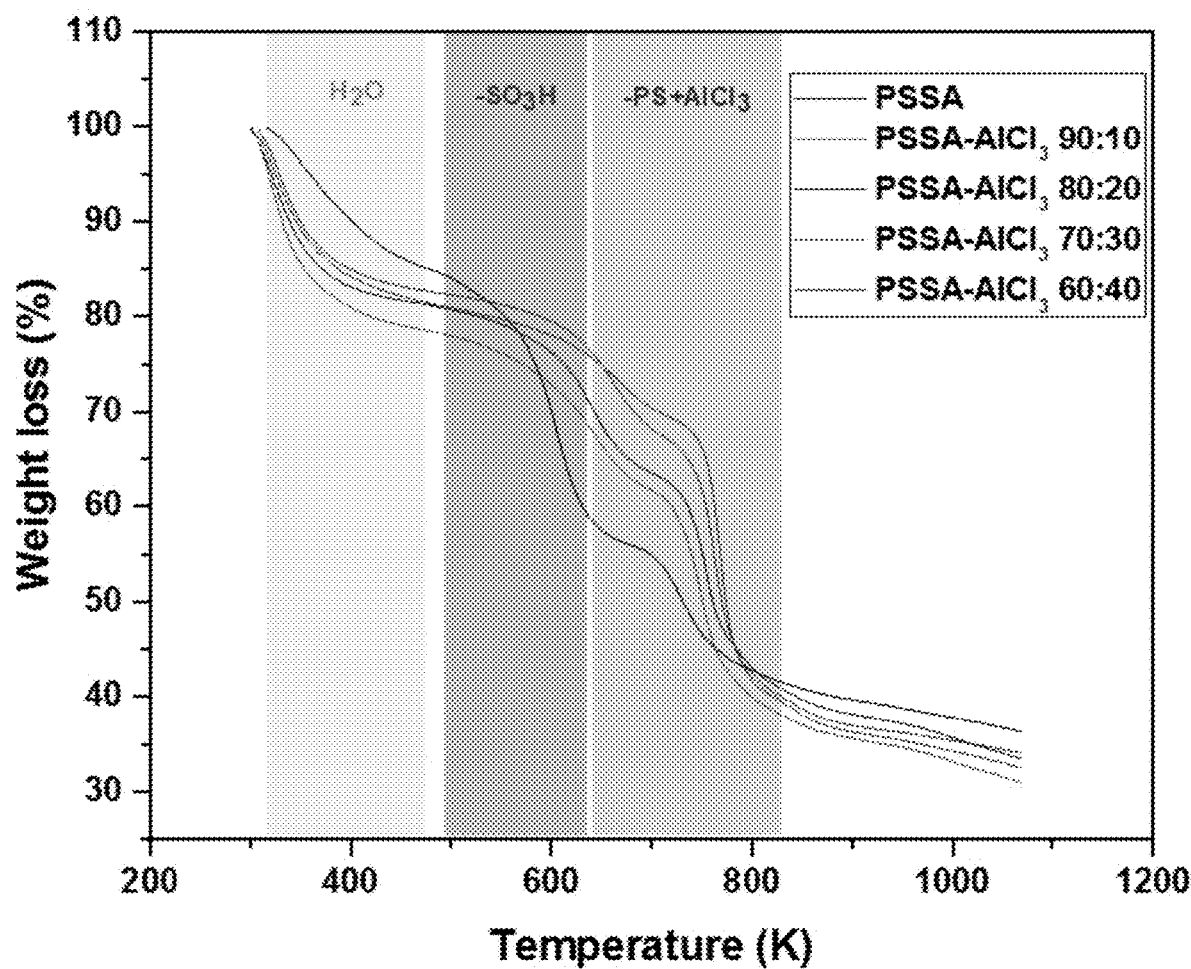
FIG. 6: Weight loss % vs temperature of PSSA and series of PSSA-$AlCl_3$ catalysts.
Figure 7:
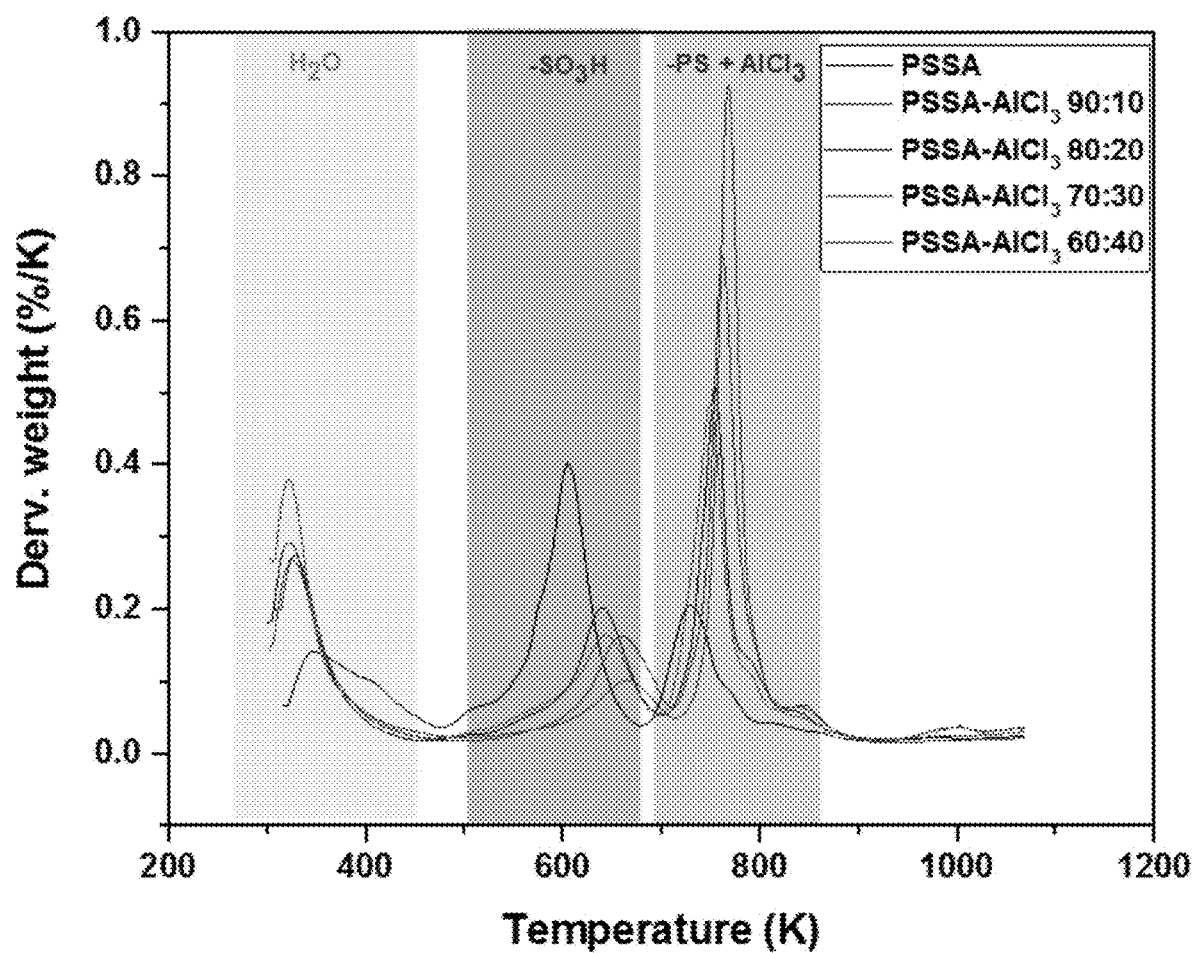
FIG. 7: Derivative weight loss % vs temperature of PSSA and series of PSSA-$AlCl_3$ catalysts.

FIGS. 6-7 compare the results obtained from TGA analysis of PSSA and the series of PSSA-AlCl₃ catalysts. The weight loss curves for PSSA-AlCl₃ catalysts look similar. The decomposition of polymers containing larger amounts of Lewis acid sites happens at higher temperatures. Without wishing to be bound by theory, it is believed this is because of the higher stability of these structures due to their crosslinked nature.

In addition, it can also be observed that the amount of water in PSSA-AlCl₃ catalysts is larger than that of PSSA. The differences are more easily observed in FIG. 7, which represents the derivative weight loss for PSSA and series of PSSA-AlCl₃ catalysts. When compared with PSSA, curves of PSSA-AlCl₃ catalysts are displaced to higher temperatures, which indicates a higher stability of those materials. In addition, it can be observed that the evolution between 250-400° C., corresponding to the decomposition of —SO₃H groups in PSSA, is shifted to higher temperatures when AlCl₃ is added to the catalyst. A reduction of the area of this peak is also observed due to the fact that the number of sulfonic groups is being reduced.

The last evolution, corresponding to the decomposition of the PS backbone, is also displaced to higher temperatures. The larger area of this peak on PSSA-AlCl₃ catalysts indicates the decomposition of the PS backbone together with the PS chains interconnected by a Lewis acid site. (See FIG. 7.)

Amount of BrøNsted Acid Sites in PSSA and PSSA-AlCl$_3$ Catalysts

The amounts of Brønsted acid sites in different PSSA-AlCl$_3$ catalysts are listed in Table 1. The amount of Brønsted acid sites is reduced by the addition of Lewis acid sites by ion exchange.

TABLE 1

Brønsted acid sites in PSSA and series of PSSA-AlCl$_3$ catalysts

| Sample (labelled as PSSA-AlCl$_3$ Brønsted:Lewis) | Estimated % of Brønsted acid sites | Estimated % of Lewis acid sites | Actual amount of Brønsted acid sites (mmol H$^+$ · g cat$^{-1}$) |
|---|---|---|---|
| PSSA | 100 | 0 | 5.40 |
| PSSA-AlCl$_3$ 90:10 | 94.7 | 5.3 | 5.00 |
| PSSA-AlCl$_3$ 80:20 | 88.9 | 11.1 | 4.63 |
| PSSA-AlCl$_3$ 70:30 | 82.4 | 17.6 | 4.60 |
| PSSA-AlCl$_3$ 60:40 | 75.0 | 25.0 | 4.44 |
| PSSA-AlCl$_3$ 50:50 | 66.7 | 33.3 | 4.38 |
| PSSA-AlCl$_3$ 40:60 | 57.1 | 42.9 | 4.11 |
| PSSA-AlCl$_3$ 30:70 | 46.2 | 53.8 | 3.94 |
| PSSA-AlCl$_3$ 20:80 | 33.3 | 66.7 | 2.71 |

$^1$H and $^{13}$C NMR of PSSA and PSSA-AlCl$_3$ Catalysts

PSSA and PSSA-AlCl$_3$ catalysts were also characterized by NMR (results not shown). No major differences were observed using this technique, only a slight reduction of the degree of sulfonation when AlCl$_3$ is added.

ATR of PSSA and PSSA-AlCl$_3$ Catalysts

Figure 8:
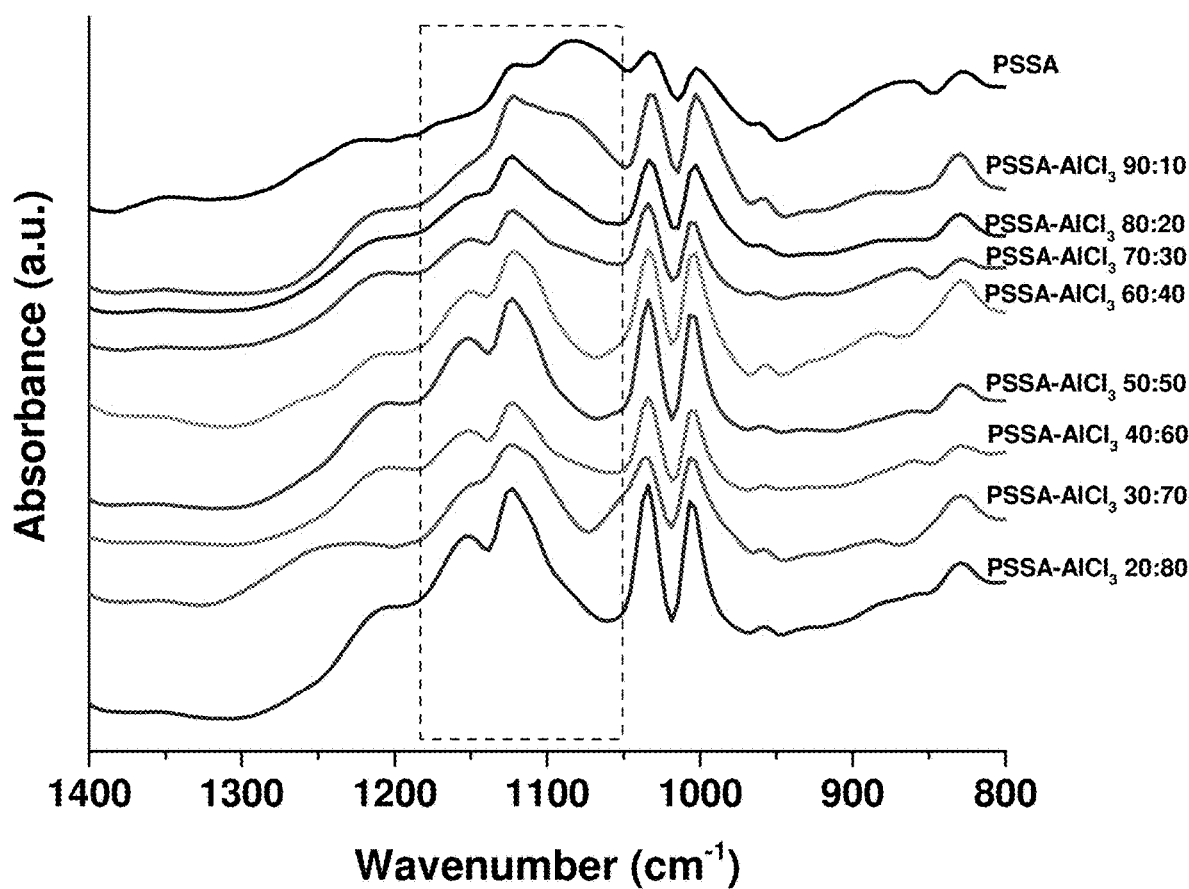
FIG. 8: ATR spectra of PSSA and series of PSSA-$AlCl_3$ catalysts.

FIG. 8 compares the ATR spectra obtained for PSSA and series of PSSA-AlCl$_3$ catalysts. All these spectra are very similar. The only differences are in the bands located between 1050 and 1180 cm$^{-1}$, which were assigned to S—O vibrations (~1080 cm$^{-1}$), benzene ring plane stretching (~1125 cm$^{-1}$), and ring C—H in-place bending vibrations (~1155 cm$^{-1}$), which decrease and increase their intensities respectively when the amount of Lewis acid sites is increased.

Inductively Coupled Plasma-Mass Spectrometry (ICP-MS) Analysis of PSSA and PSSA-AlCl$_3$ Catalysts Table 2 shows the amount of Al content in the catalysts prepared by ion exchange of PSSA with AlCl$_3$. The amount of Al in the catalyst increased with the amount of AlCl$_3$ used for the ion exchange.

TABLE 2

ICP-MS results of PSSA and series of PSSA-AlCl$_3$ catalysts

| Catalyst | ppb of Al (µg Al/g catalyst) estimated | ppb of Al (µg Al/g catalyst) experimental (ICP-MS) |
|---|---|---|
| PSSA-AlCl$_3$ 90:10 | 7,285 | 7,753 |
| PSSA-AlCl$_3$ 80:20 | 14,570 | 16,994 |
| PSSA-AlCl$_3$ 70:30 | 21,855 | 25,102 |
| PSSA-AlCl$_3$ 60:40 | 29,139 | 29,740 |
| PSSA-AlCl$_3$ 50:50 | 36,424 | 32,864 |
| PSSA-AlCl$_3$ 40:60 | 43,709 | 36,446 |
| PSSA-AlCl$_3$ 30:70 | 50,994 | 39,963 |
| PSSA-AlCl$_3$ 20:80 | 58,279 | 42,198 |

CONCLUSION

PSSA-AlCl$_3$ catalysts were successfully prepared by ion exchange in liquid medium. PSSA-AlCl$_3$ 20:80 exhibited the best catalytic properties in the conversion of glucose to HMF.

Figure 9A:
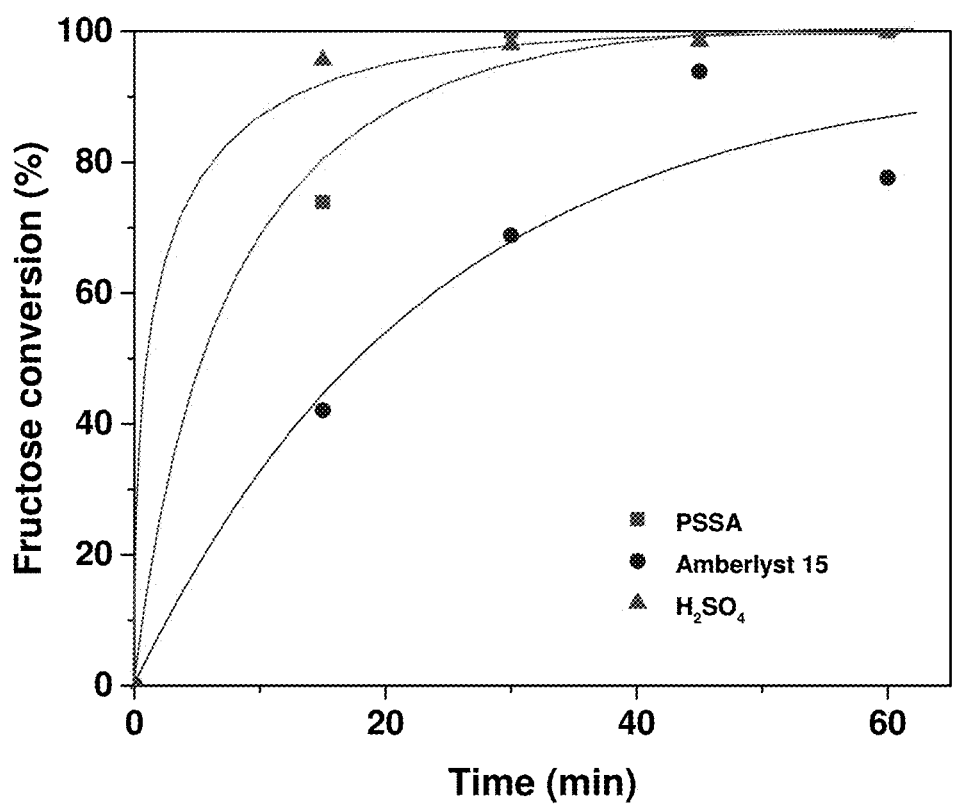
FIG. 9A-9C: Conversion of fructose to HMF with PSSA, $H_2SO_4$, and Amberlyst 15®.
Figure 9B:
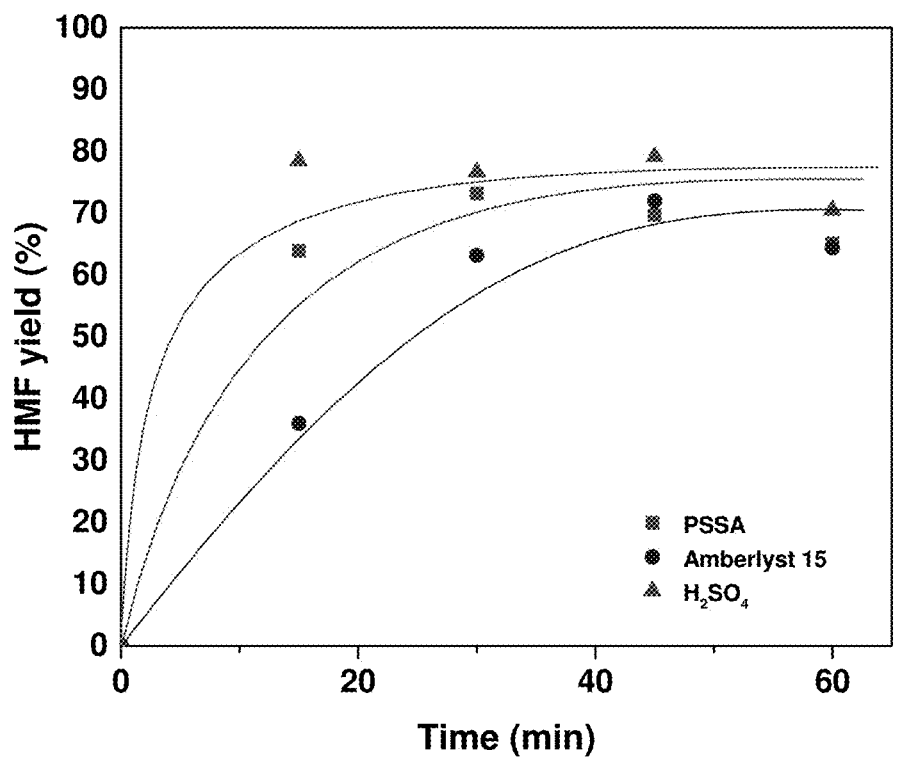
Figure 9C:
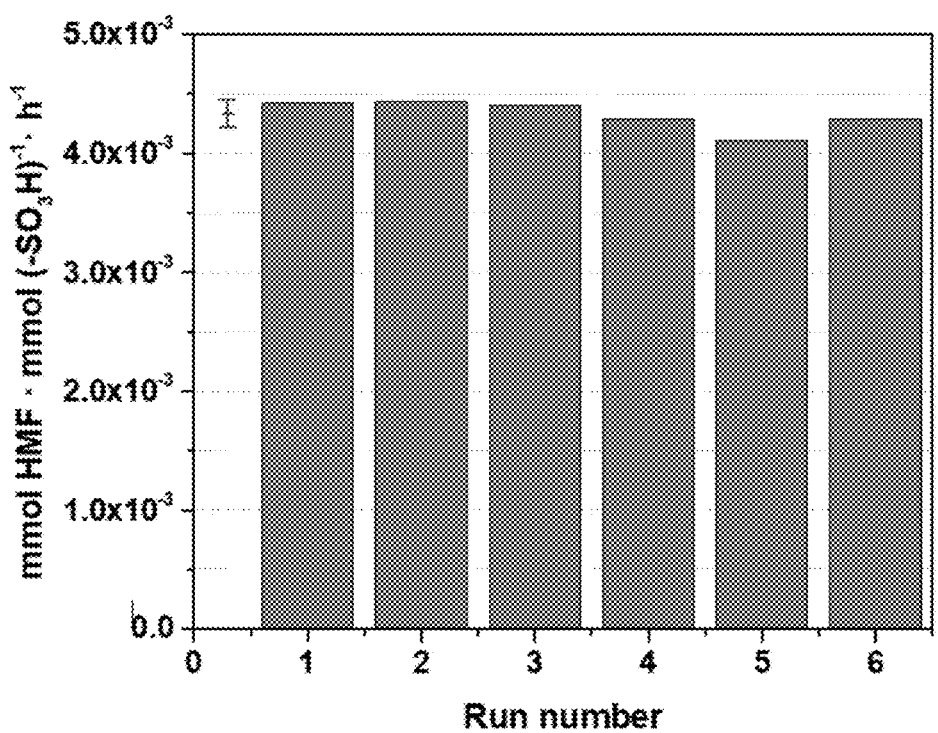

Example II—Synthesis of 5-hydroxymethylfurfural from Glucose Using PSSA-AlCl$_3$ The effectiveness of PSSA in the dehydration of fructose to HMF was evaluated. PSSA was compared with a pure homogeneous catalyst (H$_2$SO$_4$) and a heterogeneous catalyst (Amberlyst 15® sulfonic resin). To better compare the results, the same amount of sulfonic groups (—SO$_3$H) was used in each reaction. As can be seen in FIGS. 9A-9B, PSSA (which only possesses Brønsted acid sites) was comparable to H$_2$SO$_4$ in conversion of glucose to HMF.

Figure 10A:
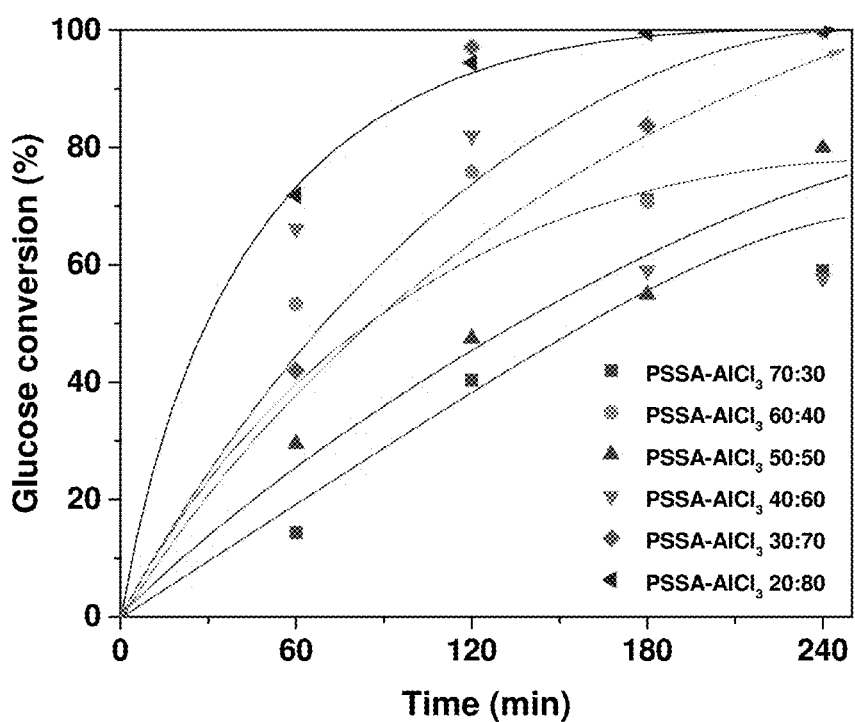
FIG. 10A-10C: Conversion of glucose to HMF with PSSA and PSSA-AlCl$_3$ catalysts.
Figure 10B:
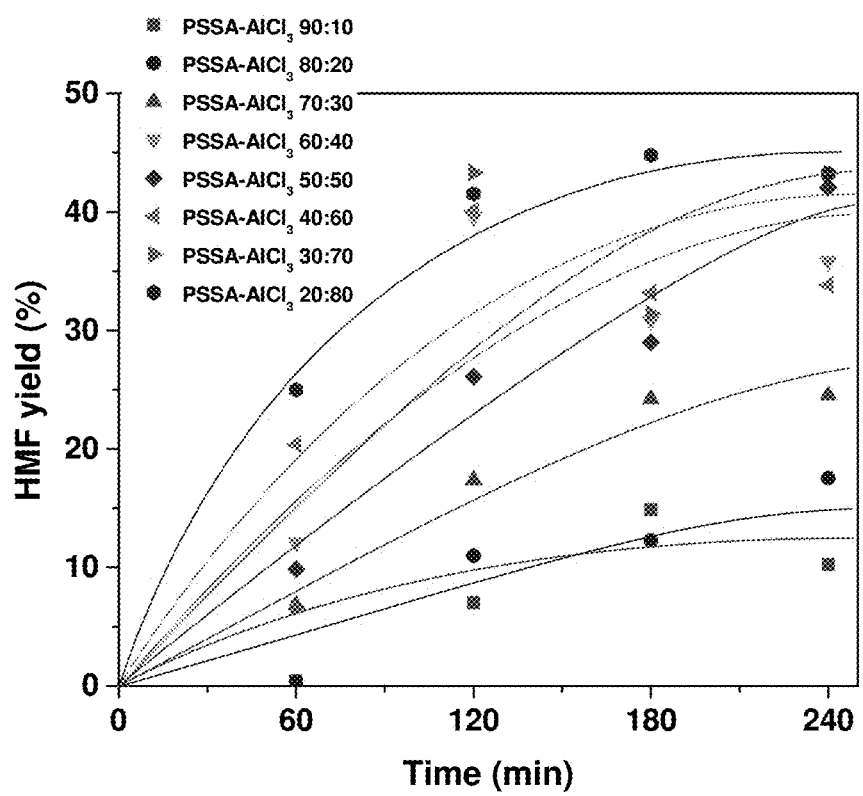
Figure 10C:
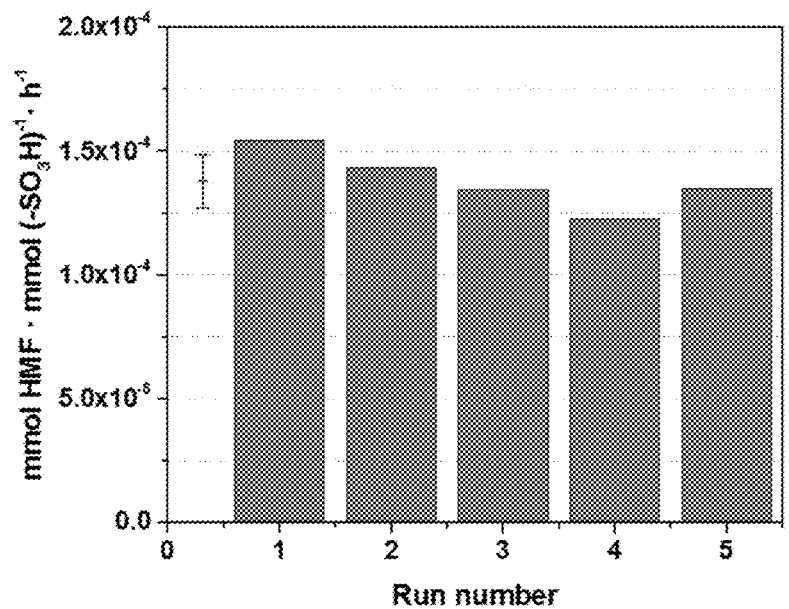

Eight catalysts with different Brønsted:Lewis acid site ratios were prepared by ion exchange of PSSA with AlCl$_3$ in alcoholic medium as described in Example I. 10, 20, 30, 40, 50, 60, 70, and 80% of the sulfonic groups in PSSA were respectively substituted by Lewis acid sites, able to carry out the isomerization of glucose to fructose. Samples were labelled as PSSA B:L, where B stands for the estimated percentage of Brønsted acid sites in the catalyst and L stands for the number of Brønsted acid sites estimatedly substituted by Lewis acid sites by ion exchange. To better compare the results, the same amount of sulfonic groups (—SO$_3$H) was used in each reaction. As seen in FIGS. 10A-10B, the addition of AlCl$_3$ contributes to an increased production of HMF. The best result was obtained with the PSSA 20:80 catalyst, which is the soluble catalyst with the highest concentration of Lewis acid sites. As seen in FIG. 10C, the PSSA-AlCl$_3$ 70:30 catalyst was reutilized for five runs without a significant decline in reaction rate. Even when the value obtained for the 4th run was smaller than the rest of the experiments, the activity on the 5th run was close to the mean value. The red line on the graph in FIG. 10C represents the mean value±standard deviation for the five runs.

This Example confirms the ability of PSSA-AlCl$_3$ to catalyze the synthesis of HMF from fructose and glucose in a one-pot synthesis. Lewis acid functionality was added to soluble PSSA while maintaining its solubility for use as a homogeneous and reusable superacid catalyst in the production of HMF from glucose. These catalysts can join the advantages of homogeneous and heterogeneous catalysts.

Certain embodiments of the compositions and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A composition comprising a compound of Formula A:

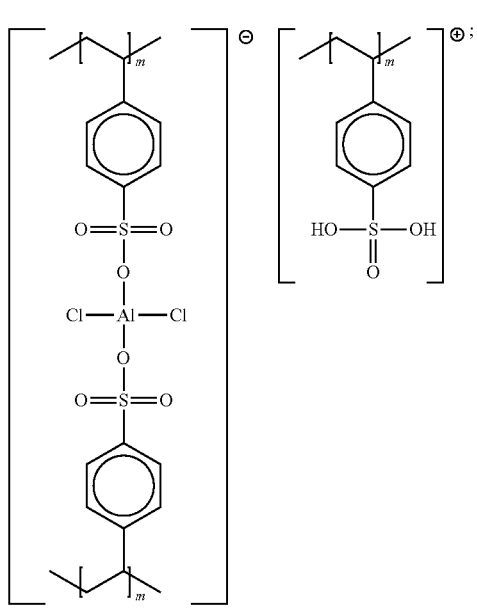

Formula A wherein m is an integer ranging from about 5,000 to about 85,000.

2. The composition of claim 1, wherein the polystyrene chain of the compound of Formula A has a molecular weight from about 10,000 Da to about 1,500,000 Da.

3. The composition of claim 1, wherein the compound of Formula A is dissolved in a polar solvent selected from the group consisting of water, gamma-valerolactone (GVL), dimethyl sulfoxide (DMSO), and DMSO-water systems.

4. The composition of claim 1, wherein the compound of Formula A is dissolved in a polar solvent comprising water, and a methyl-isobutyl ketone MIBK+2-butanol mixture is used as an organic phase for 5-hydroxymethylfurfural (HMF) extraction.

5. The composition of claim 1, wherein the compound of Formula A includes Brønsted acid sites and Lewis acid sites at an estimated Brønsted:Lewis ratio of up to about 90:10.

6. The composition of claim 1, further comprising nanoparticles, nanofibers, or nanosheets.

7. The composition of claim 6, wherein the nanoparticles comprise alumina or carbon.

8. The composition of claim 6, wherein the nanofibers comprise carbon.

9. The composition of claim 6, wherein the nanosheets comprise graphene.

10. The composition of claim 1, further comprising a monomer which increases the hydrophilicity of the composition.

11. A composition comprising a poly(styrenesulfonic acid)-based (PSSA) polymer compound having both Lewis acid sites and Brønsted acid sites, wherein the compound is soluble in polar solvents.

12. The composition of claim 11, wherein the compound is made by ion exchange between PSSA and one or more of $AlCl_3$, $SnCl_4$, $TiCl_4$, $BF_3$, $MoS_2$, $ZnCl_2$, $VCl_4$, $NiCl_2$, $GaCl_3$, $GeCl_4$, $AsCl_2$, $BCl_3$, $SiCl_4$, $SbCl_3$, $PCl_3$, or $Et_2AlCl_3$.

13. A method of producing a catalyst, the method comprising adding a Lewis acid to a soluble poly(styrenesulfonic acid)-based (PSSA) polymer in a liquid medium to produce a superacid catalyst,
wherein the Lewis acid is one of $AlCl_3$, $SnCl_4$, $TiCl_4$, $BF_3$, $MoS_2$, $ZnCl_2$, $VCl_4$, $NiCl_2$, $GaCl_3$, $GeCl_4$, $AsCl_2$, $BCl_3$, $SiCl_4$, $SbCl_3$, $PCl_3$, or $Et_2AlCl_3$.

14. The method of claim 13, wherein the liquid medium comprises a mixture of methanol and ethanol.

15. A method of preparing 5-hydroxymethylfurfural (HMF), the method comprising:
isomerizing glucose and dehydrating fructose with a single catalyst to produce HMF,
wherein the catalyst comprises the poly(styrenesulfonic acid)-based (PSSA) polymer compound having both Lewis acid sites and Brønsted acid sites of claim 11; and,
wherein the catalyst is made by ion exchange between PSSA and one or more of $AlCl_3$, $SnCl_4$, $TiCl_4$, $BF_3$, $MoS_2$, $ZnCl_2$, $VCl_4$, $NiCl_2$, $GaCl_3$, $GeCl_4$, $AsCl_2$, $BCl_3$, $SiCl_4$, $SbCl_3$, $PCl_3$, or $Et_2AlCl_3$.

16. The method of claim 15, wherein the catalyst comprises a compound of Formula A:

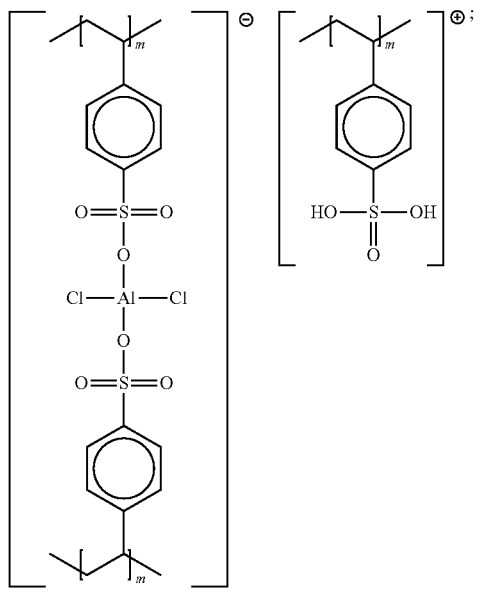

Formula A wherein m is an integer ranging from about 5,000 to about 85,000.

17. The method of claim 15, wherein the isomerization and dehydration are conducted in a solvent comprising water, gamma-valerolactone (GVL), dimethyl sulfoxide (DMSO), a water-DMSO system, or a biphasic aqueous-organic system comprising water-(MIBK+2-butanol).

18. The method of claim 15, further comprising converting the HMF into one of dimethylfuran (DMF), adipic acid, 1,6-hexanediol, levulinic acid, caprolactam, 2,5-dimethylfuran, 5-hydroxymethylfuronic acid, 3,5-dihydroxymethylfuran, 5-hydroxy-4-keto-2-pentenoic acid, or 2,5-furandicarboxylic acid (FDCA).

* * * * *

UNITED STATES PATENT AND TRADEMARK OFFICE
CERTIFICATE OF CORRECTION

| | |
|---|---|
| PATENT NO. | : 11,607,677 B2 |
| APPLICATION NO. | : 16/759065 |
| DATED | : March 21, 2023 |
| INVENTOR(S) | : Ana C. Alba Rubio et al. |

It is certified that error appears in the above-identified patent and that said Letters Patent is hereby corrected as shown below:

On the Title Page

Item (73) Assignee:
Change:
"TJie University of Toledo, Toledo, OH (US)"
To:
--The University of Toledo, Toledo, OH (US)--

Signed and Sealed this
Sixteenth Day of May, 2023

*Katherine Kelly Vidal*

Katherine Kelly Vidal
*Director of the United States Patent and Trademark Office*